United States Patent
Shellef

(10) Patent No.: US 10,365,270 B2
(45) Date of Patent: Jul. 30, 2019

(54) METHOD AND DEVICES FOR DISCHARGING CONTAMINANTS OUT OF A SEAL CHAMBER

(71) Applicant: ETTEM ENGINEERING S.A. LTD., Acco (IL)

(72) Inventor: Rammy A. Shellef, Acco (IL)

(73) Assignee: ETTEM ENGINEERING S.A. LTD., Acco (IL)

(*) Notice: Subject to any disclaimer, the term of this patent is extended or adjusted under 35 U.S.C. 154(b) by 169 days.

(21) Appl. No.: 14/741,005

(22) Filed: Jun. 16, 2015

(65) Prior Publication Data

US 2016/0010671 A1    Jan. 14, 2016

(30) Foreign Application Priority Data

Jul. 10, 2014  (IL) .......................................... 233615

(51) Int. Cl.
  *F15D 1/00*      (2006.01)
  *F16J 15/18*     (2006.01)
  (Continued)

(52) U.S. Cl.
  CPC ............ *G01N 33/542* (2013.01); *C09B 11/02* (2013.01); *C09B 69/103* (2013.01); *C09K 9/02* (2013.01);
  (Continued)

(58) Field of Classification Search
  CPC .... F15D 1/0025; F15D 1/0055; F17C 13/002; F04D 7/04; F04D 29/708; F04D 29/70;
  (Continued)

(56) References Cited

U.S. PATENT DOCUMENTS 2,769,390 A    11/1956  Heimbuch
3,070,028 A *  12/1962  Loy ....................... F04D 29/126
                                                        277/348
(Continued)

FOREIGN PATENT DOCUMENTS

EP           2458225 A1    5/2012

OTHER PUBLICATIONS

Extended European Search Report dated Dec. 8, 2015, issued in counterpart European Application No. 15175236.7.
(Continued)

*Primary Examiner* — David C Mellon
*Assistant Examiner* — Liam Royce
(74) *Attorney, Agent, or Firm* — Holtz, Holtz & Volek PC

(57) ABSTRACT

A method and an ejection device are provided for discharging contaminants out of a seal chamber of a rotating-fluid machine driving a main flow of contaminated fluid. The ejection device incorporates an obstacle for arresting a portion of the flow in the seal chamber to stagnation pressure, whereby a zone of fluid at stagnation pressure is created. A discharge passage is disposed in the seal chamber adjacent to a region of concentration of contaminants and in the zone of stagnation pressure created by the obstacle, whereby contaminants are pumped out via the discharge passage into the main driven flow. The discharge passage is disposed upstream of the obstacle and provides fluid communication between the seal chamber and a process side of the machine. The method and the ejection device are operative with a machine driving fluid in clockwise direction, in counterclockwise direction, and in both clockwise and counterclockwise direction.

13 Claims, 10 Drawing Sheets

(51) Int. Cl.

| | | |
|---|---|---|
| *F04D 7/04* | (2006.01) | |
| *F04D 29/70* | (2006.01) | |
| *F16J 15/324* | (2016.01) | |
| *F16J 15/40* | (2006.01) | |
| *F16J 15/34* | (2006.01) | |
| *F04D 29/10* | (2006.01) | |
| *G01N 33/542* | (2006.01) | |
| *G01N 33/58* | (2006.01) | |
| *C12Q 1/6818* | (2018.01) | |
| *C09B 11/02* | (2006.01) | |
| *C09B 69/10* | (2006.01) | |
| *C09K 9/02* | (2006.01) | |
| *C09K 11/06* | (2006.01) | |
| *G01N 33/52* | (2006.01) | |
| *B82Y 15/00* | (2011.01) | |

(52) U.S. Cl.
CPC ............ *C09K 11/06* (2013.01); *C12Q 1/6818* (2013.01); *G01N 33/52* (2013.01); *G01N 33/582* (2013.01); *B82Y 15/00* (2013.01); *C09K 2211/1416* (2013.01); *C09K 2211/1425* (2013.01); *C12Q 2565/107* (2013.01)

(58) Field of Classification Search
CPC ....... F04D 29/106; F04D 29/10; F16J 15/406; F16J 15/3404; F16J 15/324
See application file for complete search history.

(56) References Cited

U.S. PATENT DOCUMENTS

| | | | |
|---|---|---|---|
| 4,721,313 A | 1/1988 | Pennink | |
| 4,872,690 A | 10/1989 | Dunford | |
| 5,167,418 A | 12/1992 | Dunford | |
| 5,553,868 A | 9/1996 | Dunford | |
| 7,121,551 B2 | 10/2006 | Dunford et al. | |
| 2009/0045589 A1* | 2/2009 | Patton | F04D 29/106 277/516 |
| 2013/0243568 A1 | 9/2013 | Stahle et al. | |
| 2013/0243634 A1 | 9/2013 | Ciro et al. | |
| 2014/0175312 A1* | 6/2014 | Jamison | F16K 1/34 251/129.15 |
| 2015/0322968 A1* | 11/2015 | Allaire | F04D 29/708 415/1 |
| 2016/0136655 A1* | 5/2016 | Peterson | F16K 31/0644 137/544 |

OTHER PUBLICATIONS

European Notice of Allowance dated Apr. 19, 2018 issued in counterpart European Application No. 15175236.7.
Canadian Search Report dated Jul. 25, 2016 issued in counterpart Canadian Application No. 2916629.

\* cited by examiner

METHOD AND DEVICES FOR DISCHARGING CONTAMINANTS OUT OF A SEAL CHAMBER

TECHNICAL FIELD

The embodiments described hereinbelow relate to the field of dynamic axisymmetric work-absorbing turbomachinery, also referred to as rotating-fluid machines, and in particular to methods and devices for the removal of contaminants out of a seal chamber of a rotating-fluid machine.

BACKGROUND

Technical Problem

The problem is that available devices for removing contaminant particulates out of an annular seal chamber are direction-of-flow dependent, thus for use with either a clockwise or a counterclockwise direction of flow of the fluid driven by a rotating-fluid machine. The fact that the available devices have direction dependent geometries requires the use of a specific device that is adapted to the direction of rotation of flow of the machine. In addition, a specific device dedicated to one direction of rotation of flow of the machine is prone to being mistakenly installed in machine driving fluid in the opposite direction.

Solution to Problem

Advantage is taken from fluid dynamic equations related to the Pitot effect to provide a pumping mechanism for which a simple ejection device is practically independent from the direction of rotation of the driven fluid. Stopping a portion of the contaminated fluid rotating in the annular seal chamber is used to create a local zone of fluid at stagnation pressure. The stagnation pressure is locally higher than the static pressure within the seal chamber or in the process side of the machine. The zone at stagnation pressure is used for pumping contaminants out of the seal chamber through a discharge passage, which is disposed upstream of the zone at stagnation pressure. At least a portion of the discharge passage is disposed in the zone at stagnation pressure. The zone at stagnation pressure thus pumps contaminants through the discharge passage, into the process side and into the main flow of driven fluid.

The fluid pumping mechanism is implemented as a disk structure which is configured as an ejection device. The disk structure may be the same for a clockwise direction, a counterclockwise direction, and both the clockwise and counterclockwise directions of the main flow of driven fluid. At least one discharge passage opened in a disk structure forms an ejection device which permits operation with one direction of flow of the liquid. However, at least two such discharge passages opened in a disk structure are necessary for the implementation of an ejection device that is bidirectional, thus independent of the direction of flow of the main driven fluid.

Advantageous Effects of Invention

With the embodiments described hereinbelow, the fluid flow mechanism and the disk structure of the new ejection device are practically the same for a clockwise direction, a counterclockwise direction, and both the clockwise and counterclockwise directions. One discharge passage open in the disk structure limits the ejection device for operation with either a clockwise direction or a counterclockwise direction of machine driven flow. However, two such discharge passages may allow the implementation of an ejection device capable of operation with both a clockwise and a counterclockwise direction of main flow of machine driven liquid. The necessary pumping effect is thus provided by an ejection device having a direction independent geometry. Hence, there is formed a direction independent ejection device that is self-adaptable to the direction of rotation of the main flow of fluid.

Furthermore, the ejection device is simple to produce and may be implemented by use of a variety of manufacturing processes, including milling, forging, casting, injection molding, sintering, and 3-D printing.

Moreover, the ejection device may be manufactured out of multiple materials ranging from metals to synthetics such as plastic materials.

DESCRIPTION OF RELATED ART

It is well known per se that keeping seal cavities clean from contaminants, including particles and particulates of abrasive nature, is beneficial to increase the longevity of seals. Therefore, some attempts have been made to provide solutions.

Known devices are recited in U.S. Pat. Nos. 4,872,690 and 5,167,418, both to J. R. Dunford, and teach respectively, a seal cavity protector and a grit protector, both depending on and operative with one direction of rotation of the fluid, and both having vent passages.

U.S. Pat. No. 5,553,868 to J. R. Dunford teaches a throat cavity seal bushing using a spiral groove or multiple spiral grooves which are configured to guide the abrasives inwardly towards the shaft for being removed by a flow of clean flush injected into the seal cavity. As a further bushing variant, U.S. Pat. No. 7,121,551 to J. R. Dunford et al., discloses two such bushings operative in mutual association and allowing to switch between the use of a mechanical seal or conventional packing without having to discard the primary seal cavity protector.

U.S. Pat. No. 5,167,418 to J. R. Dunford recites a grit protector including at least one vent passage between a flange and an axial section for passing fluids and contaminants out of a cavity. The vent passage has a flap. Practically, the vent passage scoops fluid.

U.S. Pat. No. 4,721,313 to Hans Pennink, discloses a labyrinth seal having bleed holes. A raise lip is added downstream of the bleed hole entrance to intercept entrained particle in the fluid stream and direct them into the bleed hole. The internal passage is vented to an area of lower pressure, such as an external suction pump.

However, the four US Patents to J. R. Dunford and to J. R. Dunford et al. are dependent on and are operative with one direction of flow of the fluid. Therefore, these four US Patents recite direction dependent geometries which are dependent on the direction of rotation of the driven fluid.

It would therefore be advantageous to provide an ejection device that is self-adaptable to the direction of rotation of the driven fluid.

SUMMARY

There is described a method and an ejection device for discharging contaminants out of a seal chamber of a rotary machine which rotates and drives a main flow of contaminated fluid. To this end, at least one zone of fluid at stagnation pressure is created in the seal chamber. The stagnation pressure created in the at least one zone ejects the contaminants out of the seal chamber through at least one discharge passage and into the main flow.

There is also described a method and an ejection device for discharging or ejecting contaminants out of a seal chamber of a machine which rotates and drives a main flow of contaminated fluid. For this purpose, there is provided a disk structure for closing a proximal region of the seal chamber. The disk structure includes an obstacle for creating at least one zone of fluid at stagnation pressure in the seal chamber when the seal chamber is closed. Furthermore, to configure the disk structure into an ejection device, at least one discharge passage is opened therein to be to be disposed upstream of the obstacle in at least a portion of the at least one zone at stagnation pressure. Closing the seal chamber with the disk structure ejects contaminants thereout through the at least one discharge passage, whereby the contaminants are pumped back into the main flow.

There is embodied an ejection device wherethrough passes a pump shaft. The ejection device closes a proximal region of a seal chamber of a rotary machine. The rotary machine is configured for driving a main flow of fluid holding contaminants. The ejection device incorporates therein an obstacle which is disposed in the proximal region of the seal chamber to create at least one zone of fluid at stagnation pressure. The ejection device also has at least one discharge passage which is disposed entirely or in portion, in the at least one zone at stagnation pressure. The at least one discharge passage is configured to couple the proximal region and the main flow in fluid communication. As a result, the stagnation pressure pumps contaminants out of the seal chamber and into the main flow via the discharge passage.

In an embodiment, a disk structure configurable into an ejection device is configured to close a proximal region of a seal chamber and to discharge contaminants out of a seal chamber. The seal chamber is disposed in a machine rotating fluid that is driven into a main flow. The disk structure incorporates therein at least one flow blocking face which is disposed in the proximal region of the seal chamber. The at least one flow blocking face is configured to create, relative to a clockwise or a counterclockwise direction of rotation of the main flow, a respective zone of fluid at stagnation pressure. At least one discharge passage is opened in the disk structure, and is disposed in at least a portion of the respective zone that ejects contaminants into the main flow. Thereby, there is formed an ejection device that is self-adaptable to the direction of rotation of the main flow of fluid.

BRIEF DESCRIPTION OF DRAWINGS

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements, or parts that appear in more than one figure are preferably labeled with a same or similar number in all the figures in which they appear, in which.

DESCRIPTION OF EMBODIMENTS

The wording 'incorporated in' or 'incorporate therein' and derivations thereof are meant to be understood as 'integrated in, or 'supported by', or 'included in' with respect to the various embodiments described in the present disclosure.

Figure 1:
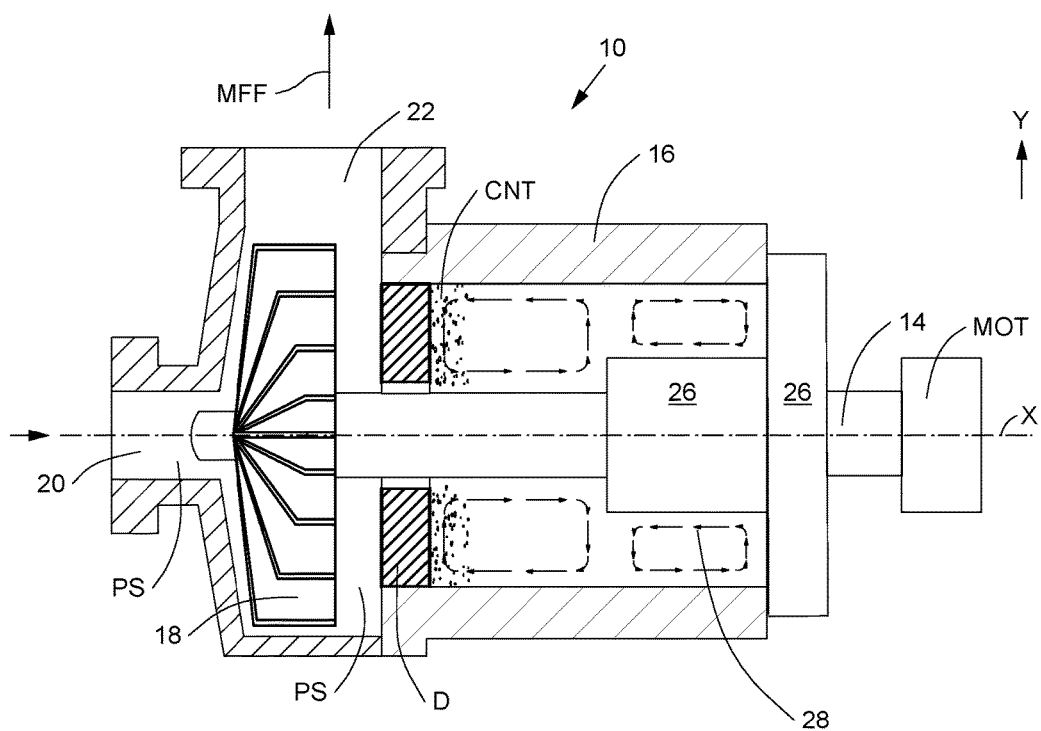
FIG. 1 schematically illustrates a cross-section of a typical rotary fluid flow machine, FIG. 2 schematically presents a detail of a typical seal chamber of the machine shown in FIG. 1.

FIG. 1 schematically illustrates a cross-section of a known dynamic axisymmetric work-absorbing turbomachine, such as a rotary machine driving fluid, or a piece of rotary equipment, that may simply be referred to as a machine 10. A well-known, typical example of such a machine is a compressor or a pump 10, suitable for use of the method and of the device, which is not shown in FIG. 1 but is described hereinbelow. FIG. 1 depicts a machine 10 such as a pump 10 driven via a pump shaft 14, or shaft 14, for example by an electric motor MOT. The pump shaft 14 is typically supported by suitable bearings, which are not shown in the Figs. The pump shaft 14 is rotationally coupled to a centrifugal impeller 18 which when in rotation, draws fluid into the pump 10 through a pump suction inlet 20. The ingested fluid is discharged out of the pump 10, through a radially or tangentially disposed pump discharge outlet 22, into a main flow MFF of fluid.

The pumped fluid, forming the main flow MFF of fluid, or main flow MFF, may be an industrial fluid possibly polluted by solid particle contaminants CNT. In the present description, the words 'contaminants', 'contaminated' or derivations thereof are accepted as meaning 'including foreign particles' such as sand or of intrinsic nature such as process slurry, as well as particulates of abrasive nature. The main flow MFF of contaminated fluid conveys contaminated particles or contaminants CNT that are detrimental to the operational life cycle of rotary fluid machines 10 and in particular to their sealing devices mounted in their respective seal chambers 28.

For the sake of orientation, the pump shaft 14 is regarded as being disposed along a longitudinal axis X of the pump 10 and the pump suction inlet 20 is viewed as being disposed proximally relative to the distal seal(s) assembly 26. The main flow MFF of pumped fluid, or driven fluid, the pump suction inlet 20, the centrifugal impeller 18, and the pump discharge outlet 22 are considered as being disposed on the process side PS which is proximal to the housing 16 of the pump or machine 10.

Figure 2:
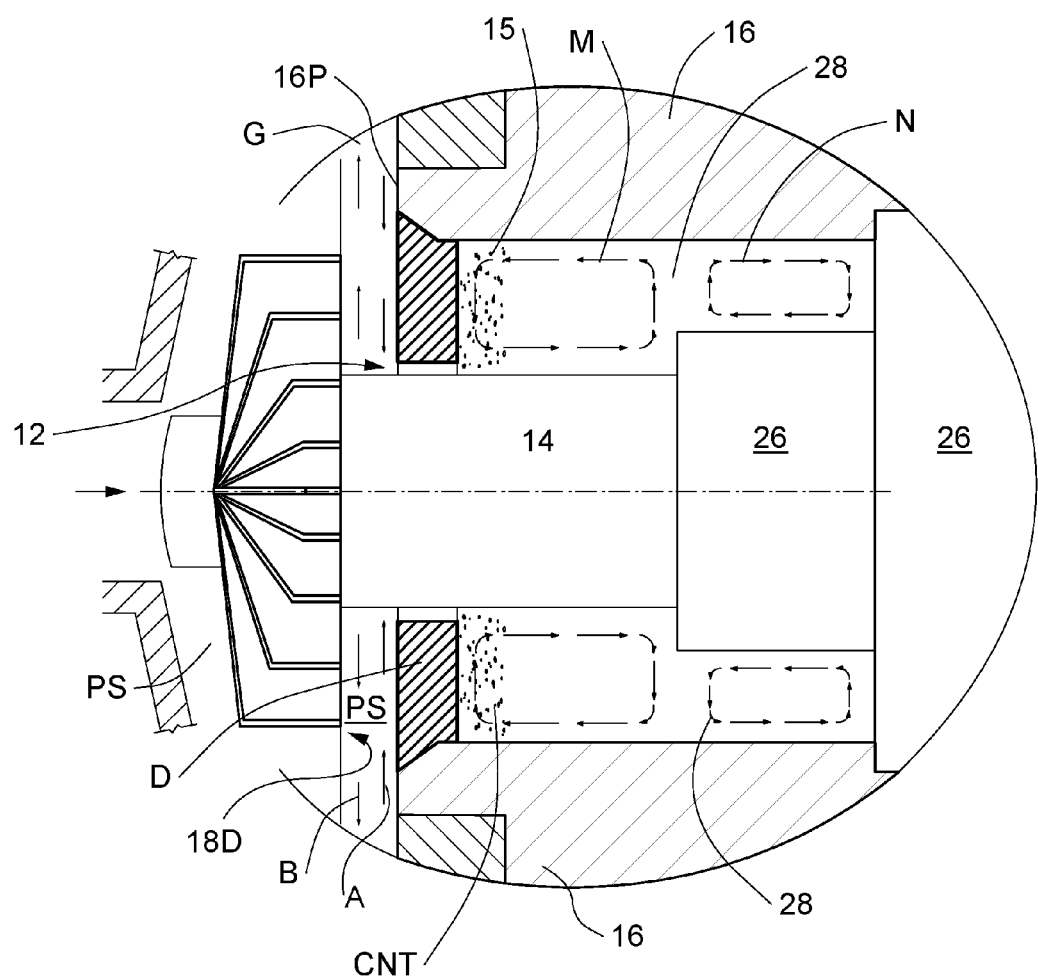

FIG. 2 schematically depicts a detail of a typical seal chamber 28 and of the machine 10 shown in FIG. 1. Such a seal chamber 28 is defined by the pump shaft 14, the pump housing 16 which surrounds a portion of the shaft 14, a seal(s) assembly 26 which contacts the shaft 14 at the distal end of the seal chamber 28, and a proximal device D. The device D, such as a protector or a bushing D, has a shaft opening 12 wherethrough the pump shaft 14 passes, as recited in the background art. Typically, the device D is disposed flush with the proximal exterior face 16P of the housing 16. The process side PS extends proximally away from the exterior face 16P of the housing 16.

FIG. 2 further illustrates counter currents, which are a spiral flow that is set up in the process side PS by the rotating pump shaft 14 and by the main flow MFF of pumped fluid. The counter currents A shown by the arrows marked A, flow spirally inwardly toward the axis X and into the seal chamber 28 through the shaft opening 12 which is disposed in the proximal exterior face 16P of the housing 16. Those counter currents A flowing on the process side PS, carry an average amount of contaminants CNT such as abrasive particulate material, and when such contaminants CNT enter the seal chamber 28, damage may be caused to the seals assembly 26.

Within the seal chamber 28, the primary flow is for example a clockwise vortex concentric to the shaft 14. However, fluid generally also flows in a proximal toroidal pattern of secondary flow SCND along a path shown by the arrows M and in a distal toroidal secondary counter-flow pattern along a path shown by the arrows N. In operation, relative to the ingested fluid which carries an average concentration of contaminants CNT, there is created a higher concentration of contaminants CNT that accumulate in the most proximal region 15 of the seal chamber 28.

With the embodiments described hereinbelow, such higher concentration of particulate contaminants CNT may be pumped out of the seal chamber 28 by operation of an ejection device 40. The ejection device 40 may be appropriately disposed and configured to close the proximal region 15 of the seal chamber 28. The operation of the ejection device 40 benefits from a fluid flow mechanism based on the Pitot effect described hereinbelow with respect to an ideal fluid which is selected for ease of description. In reality, a contaminated fluid CNT practically approximates an ideal fluid.

Reference is now made to the Bernoulli principle and to the Pitot effect.

The Bernoulli principle states that in a constant flow of ideal fluid, ignoring gravity, the absolute total pressure is constant, or $$P_{total} = \text{Constant} = P_{static} + P_{dynamic} = P_{static} + \tfrac{1}{2}\rho V^2 \quad (\text{equ. 1})$$

where $\tfrac{1}{2}\rho V^2$ is the dynamic pressure and where
$P_{total}$ is the absolute total stagnation pressure,
$P_{static}$ is the absolute static ambient pressure,
$P_{dynamic}$ is the dynamic pressure $\tfrac{1}{2}\rho V^2$
$\rho$ is the density of the fluid, and
V is the velocity of the fluid.

However, when the flow of fluid is brought to standstill, say when impinging on an obstacle, such as a ridge for example, the stopped flow of fluid comes to stagnation at the point of impingement. This is the so called Pitot effect. For visual illustration and ease of description, one may consider an ideal fluid flowing in a straight portion of a channel CHN.

Figure 3:
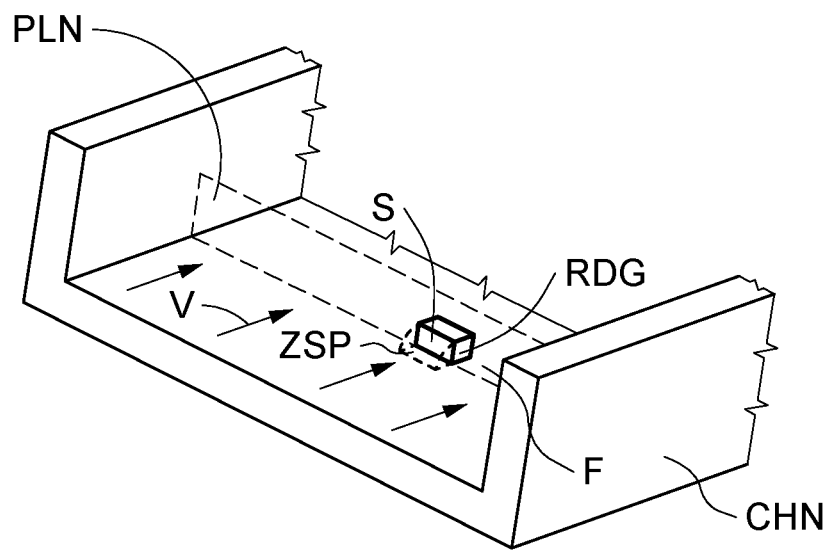
FIG. 3 depicts a channel wherein an incompressible fluid flows.

FIG. 3 depicts a channel CHN wherein an ideal fluid flows at velocity V, and where the pressure is measured at two points, namely points F and S, which are disposed in a plane PLN perpendicular to the direction of flow. F is a point in the free flow and S is a point at stagnation on a ridge RDG which locally blocks the flow of fluid.

According to equ. 1, at point F in the free flow, the pressure is $$P_{Ftotal} = P_{Fstatic} + \tfrac{1}{2}\rho V^2 \quad (\text{equ. 2})$$

and at the stagnation point S, the pressure is $$P_{Stotal} = P_{Sstatic} = P_{Sstagnation} \quad (\text{equ. 3})$$

because at velocity V=0 of the fluid at stagnation, there is no dynamic pressure.

Since the total pressure remains constant at the points F and S which are disposed in the plane PLN, $P_{Ftotal} = P_{Stotal}$, or $$P_{Sstagnation} = P_{Fstatic} + P_{Fdynamic} \quad (\text{equ. 4})$$

This means that at the stagnation point S on the ridge RDG, the static pressure is greater by $P_{Fdynamic}$, or $\tfrac{1}{2}\rho V^2$, than the static pressure at point F.

In FIG. 3 at point S, a local zone ZSP at stagnation pressure thus builds up upstream in front of the ridge RDG. One may now consider FIG. 4 which depicts how advantage is taken of the zone ZSP at higher pressure, i.e. at stagnation pressure, to practically pump fluid.

Figure 4:
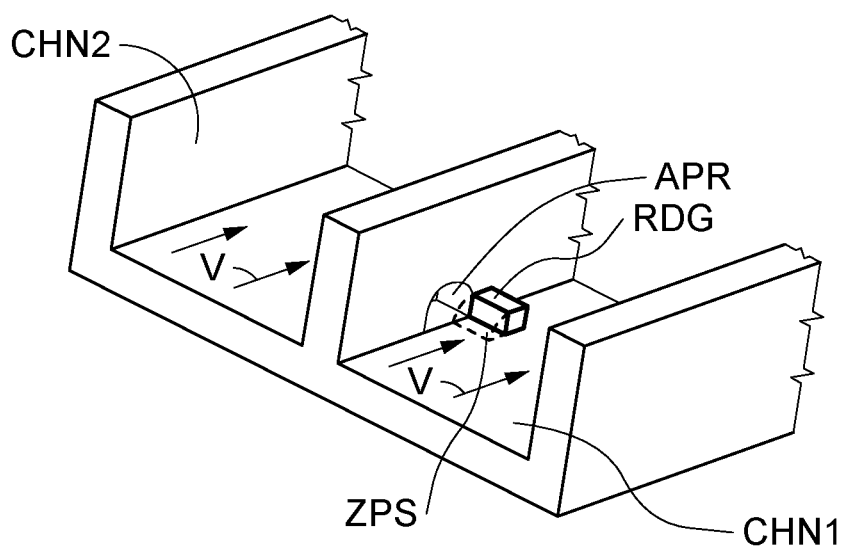
FIG. 4 shows the channel of FIG. 3 with a separation wall.

FIG. 4 shows the channel CHN of FIG. 3 wherein a wall W is disposed in abutment with the bottom of the channel CHN and with the ridge RDG, whereby the channel CHN is divided into two parallel channels, namely channels CHN1 and CHN2. The same flow of fluid at velocity V runs in both channels but in channel CHN1 there is a zone at stagnation pressure ZSP in front of, thus upstream, of the ridge RDG.

As depicted in FIG. 4, an opening or aperture APR may be created in the wall W in the zone ZPS of fluid at stagnation pressure, which aperture APR permits fluid communication between both parallel channels CHN1 and CHN2. Both channels CHN1 and CHN2 have the same static pressure in free flow. In the zone ZSP at stagnation pressure, the pressure is higher than the static pressure in the free flow of both channels CHN1 and CHN2. Hence, the higher stagnation pressure of the zone ZSP residing in the first channel CHN1 will pump fluid into and through the aperture APR, to the other side of the wall W and into the second channel CHN2. A portion of the flow of fluid is thus pumped out of the first channel CHN1 by the higher stagnation pressure of the zone ZSP against the lower static pressure in the second channel CHN2. That is to say that based on the Pitot effect, the ridge RDG is instrumental in the derivation of a pressure differential out of the flow of fluid. The function of the ridge RDG is to arrest the flow to the velocity V=0. The zone ZSP exerts pressure in all directions, including towards the direction of the aperture APR wherethrough a portion of the fluid is driven out of the channel CHN1 and into the second channel CHN2. However, the ridge RDG is not dedicated to be operative as a mechanical guide that is erected to deflect the direction of the flow and guide the fluid. Practical implementations of the Pitot-effect-based pumping effect for operation with rotary fluid machines 10 are described hereinbelow.

Exemplary Embodiments

Figure 5:
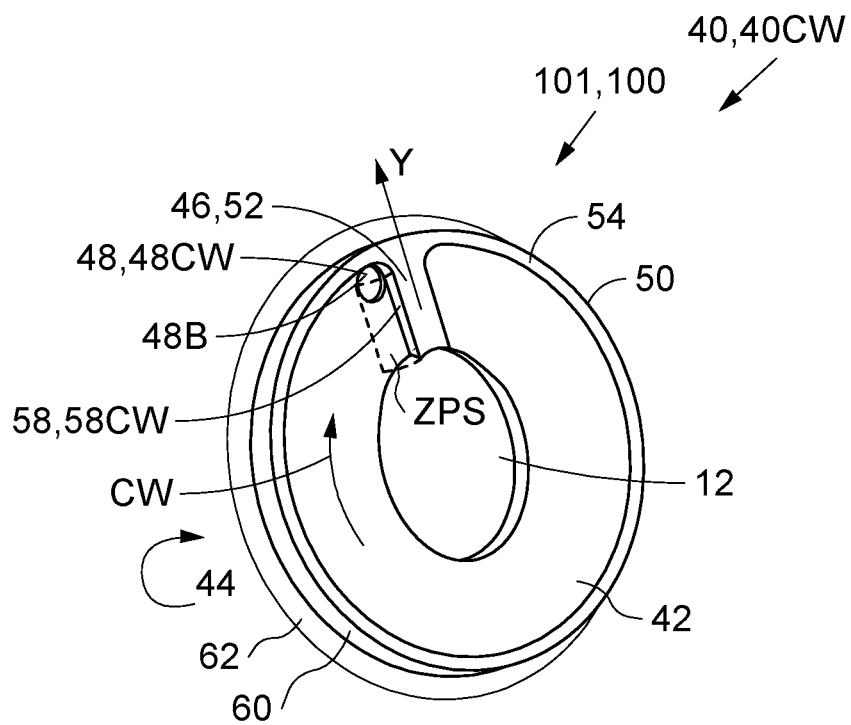
FIGS. 5 and 6 illustrate a first exemplary embodiment of an ejection device.
Figure 6:
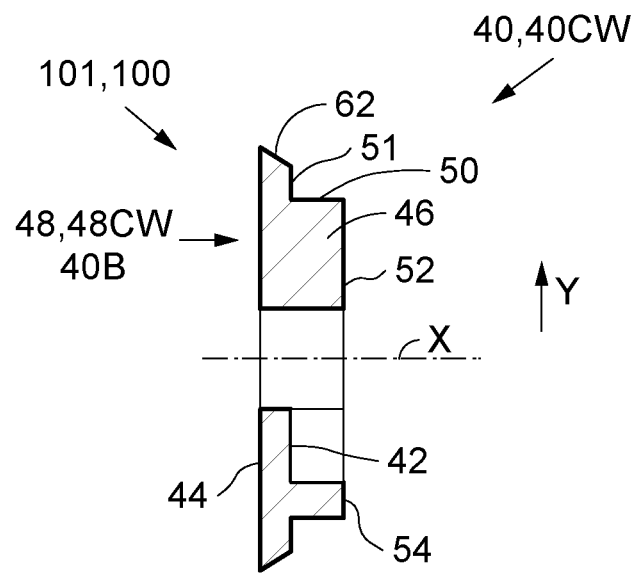
Figure 7:
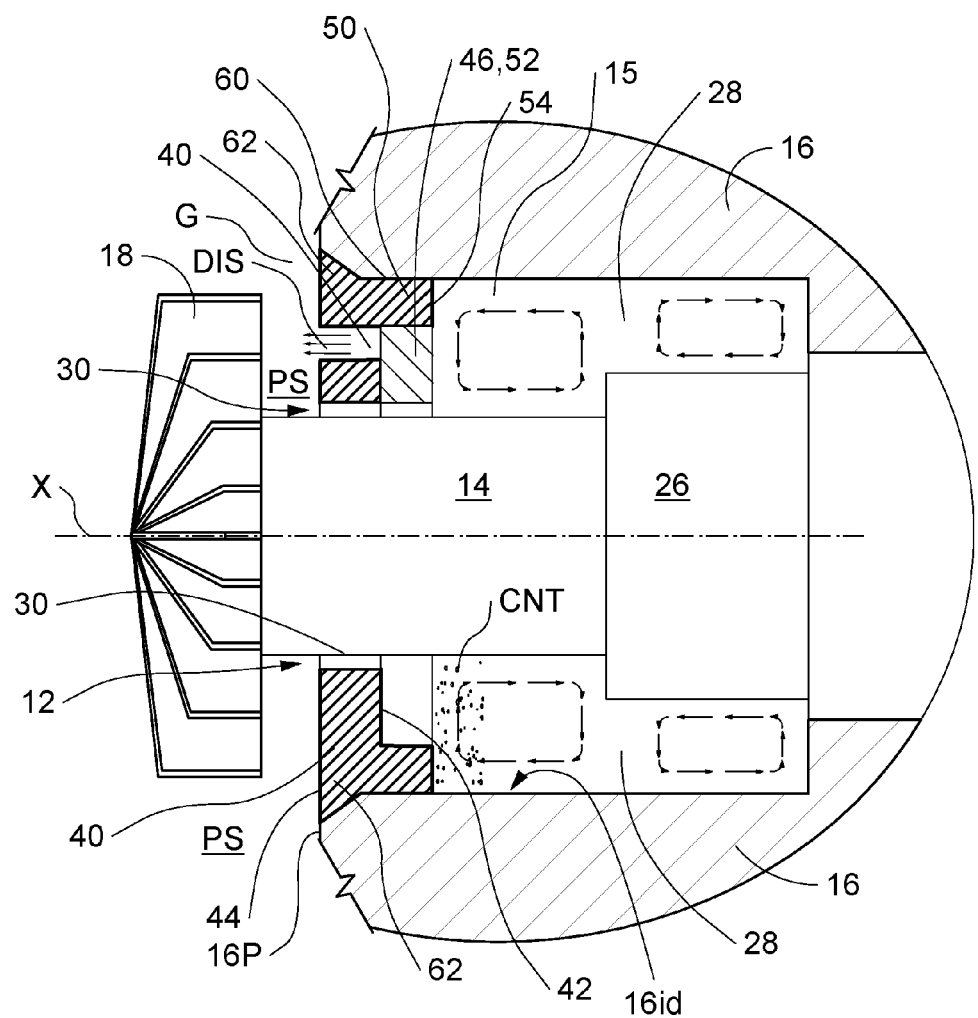
FIG. 7 depicts an ejection device mounted in a machine.

Three exemplary embodiments of a disk structure 100 which is configured as an ejection device 40 are illustrated in FIGS. 5 to 9. As described hereinbelow, a disk structure 100 includes an obstacle and may be configured into an ejection device 40 by the opening therein of at least one discharge passage 48. FIGS. 5 and 6 illustrate a first exemplary embodiment 101 of an ejection device 40 for pumping contaminants CNT out of a seal chamber 28, and FIG. 7 depicts such an ejection device 40 mounted in a machine 10. In the first embodiment 101 depicted in FIGS. 5 and 6, a disk structure 100 configured as an ejection device 40CW may be adapted to operate with a main flow MFF of fluid rotating in one direction of rotation, for example in clockwise direction CW. In a second embodiment 102 shown in FIG. 8, a disk structure 100 configured as an ejection device 40CCW may work with a main flow MFF rotating in counterclockwise direction CCW of rotation, and in a third embodiment 103 presented in FIG. 9, a disk structure 100 configured as an ejection device 40-2D is accommodated to work with a main flow MFF of fluid rotating in a direction of rotation which is either one of both clockwise CW and counterclockwise direction CCW. An ejection device 40 operative in both clockwise CW and counterclockwise direction CCW may also be referred to as a bidirectional ejection device 40-2D. When reference is made to a main flow MFF that flows in both a clockwise CW and a counterclockwise CWW direction, the meaning is that the ejection device 40 is compatible with a machine 10 able to rotate and drive the main flow MFF in either one of a clockwise CW and a counterclockwise CWW direction.

FIG. 7 illustrates the operation of a machine 10 running an ejection device 40 in general, thus operative with the first, second and third embodiment, respectively 101, 102, and 103, indicated respectively as 40CW, 40CCW, and 40-2D, and described hereinbelow.

FIG. 5 is an isometric view of a disk structure 100 which is configured as the first embodiment 101 of a clockwise ejection device 40CW operative with a main flow MFF driven in clockwise direction CW. FIG. 6 is a diametrical cross-section of the clockwise ejection device 40CW cut through an obstacle 46. For the sake of ease of illustration only, the various embodiments of ejection devices 40 of the present disclosure are described and depicted as circular bodies. The same is true for disk structures 100 that are configured as ejection devices 40. In practice, the proximal side of ejection devices 40 and of disk structures 100 may be selected to have shapes other than circular.

The clockwise ejection device 40CW may have a distal circular side 42 facing the seal chamber 28, and a proximal circular side 44 which when assembled with the housing 16, is typically flush with the proximal exterior face 16P which faces the process side PS. The distal circular side 42 and the proximal circular side 44 in the various embodiments described in the present disclosure may be planar. The distal circular side 42 may include or incorporate therein an obstacle 46 shaped as a ridge 46 for example, and a discharge passage 48. The discharge passage 48 may be designated as the clockwise discharge passage 48CW when disposed upstream of the obstacle 46, to accommodate a main flow of fluid MFF which is driven in the clockwise direction CW. The ridge 46 may be shaped for example as a parallelepiped having a quadrilateral cross-section and may protrude out and away from, and be disposed radially on the distal circular side 42. Moreover, the ridge 46 may extend radially away from a circumferential rim 50 which protrudes distally away from the distal circular side 42, and extends at most up to the shaft opening 12. The proximal circular side 44 may have an exterior diameter that slopes down towards the distal circular side 42 to form a bevel 62. A step 51 may separate the bevel 62 away from the circumferential rim 50. The step 51 may be small or even nil as is usually the case. The ridge distal surface 52 which protrudes distally away from the distal circular side 42 may preferably be disposed in a plane common to the rim distal face 54, or either above thereof or below thereof. The discharge passage 48, or here the clockwise discharge passage 48CW for operation with a main flow MFF driven in the clockwise direction CW, may be disposed adjacent to, as described hereinbelow, or as shown in FIG. 5, in abutment with the circumferential rim interior 56.

Each one of the various embodiments of the discharge passage 48 described in the present disclosure, namely the clockwise discharge passage 48CW, the counterclockwise discharge passage 48CCW, and the bidirectional discharge passage 48-2D may have at least one discharge passage 48, or bore 48B passing throughout across the ejection device 40, from the distal circular side 42 to the proximal device side 44. An embodiment of the discharge passage 48 thus provides fluid communication coupling the proximal region 15 of the seal chamber 28 to the process side PS, thus in fluid communication with the main flow MFF.

Preferably, the clockwise flow blocking face 58CW is a surface disposed perpendicular the clockwise rotating primary vortex flow flowing concentric to the shaft 14 in the seal chamber 28. The clockwise blocking face 58CW is configured to locally arrest a portion of that primary vortex flow and achieve a local zone ZSP of stopped fluid at stagnation pressure. At least a portion of the clockwise discharge passage 48CW but preferably the entirety thereof, has to be disposed in the local stagnation zone ZSP for the sake of efficacy. In FIG. 5, the arrow CW indicates the clockwise direction CW of the main flow MFF. The zone ZSP of fluid at stagnation pressure is shown symbolically and is approximately delimited by dashed lines in FIG. 5. Evidently, the shape of the discharge passage 48, or clockwise discharge passage 48CW, is not limited to a circular through bore. As described hereinbelow, the discharge passage 48 may be selected to have a desired shape on condition that the selected desired shape is disposed at least partially in the zone ZSP.

FIG. 7 illustrates a cross-section of a rotary machine 10 having a seal chamber 28 wherein an ejection device 40 is disposed. For the sake of ease of explanation, the ejection device 40 is meant to represent a clockwise, an counterclockwise, and a bidirectional, ejection device, respectively 40CW, 40CCW, and 40-2D, the last two being described hereinbelow. In FIG. 7, the ejection device 40 is shown to close the proximal exterior face 16P of the housing 16, thus to close the proximal region 15 of the seal chamber 28. The rim exterior surface 60 may be fixedly coupled to the proximal portion of the seal chamber 28 in the housing interior diameter 16id. The rim bevel 62 may arrest penetration of the ejection device 40 into the seal chamber 28, for if desired, the proximal circular side 44 to be disposed for example flush with the proximal exterior face 16P of the housing 16. Evidently, the ejection device 40 may be coupled to the housing 16 by various methods and means known to those skilled in the art and need not to be described in detail.

In operation, the impeller 18 drives a main flow MFF of fluid through the pump 10, in reaction to which a rotary vortex flow occurs in the interior of the seal chamber 28, as described hereinabove with respect to FIGS. 1 and 2. The main flow MFF contains an average amount of contaminants CNT that may penetrate into the seal chamber 28 via an interstice 30 that is open between the shaft opening 12 of the ejection device 40 and the pump shaft 14. In the seal chamber 28, the contaminants CNT tend to concentrate in the proximal region 15 in which are disposed the obstacle 46 and upstream thereof, the discharge passage 48, or here, the clockwise discharge passage 48CW. The at least one zone ZSP of fluid at stagnation pressure pumps fluid out of the seal chamber proximal region 15 into the process side PS of the machine 10, through the discharge passage 48, for ejection into the main flow MFF. Hence, in the process side PS, the counter currents created by the rotating impeller 18 and the pump shaft 14 carry fluid pumped out of the proximal zone 15 for expulsion out of the machine 10 into the main flow MFF via the pump discharge outlet 22. In FIG. 7, the fluid pumped out through the clockwise discharge passage 48CW is indicated by the arrows marked DIS. The wording 'a zone ZSP' means: at least one zone ZSP.

In reaction thereto, a compensating flow of fluid carrying an average concentration of contaminants CNT enters the seal chamber 28 via the interstice 30. In the seal chamber 28, fluid with a high concentration of contaminants CNT, that is ejected out of the proximal region 15 is replaced by fluid carrying an average load of contaminants CNT, thus with less than the concentrated load of contaminants CNT. The net result is that the various embodiments of the ejection device 40 described in the present disclosure are operative to reduce and diminish the amount of contaminants CNT contained in the seal chamber 28.

Figure 8:
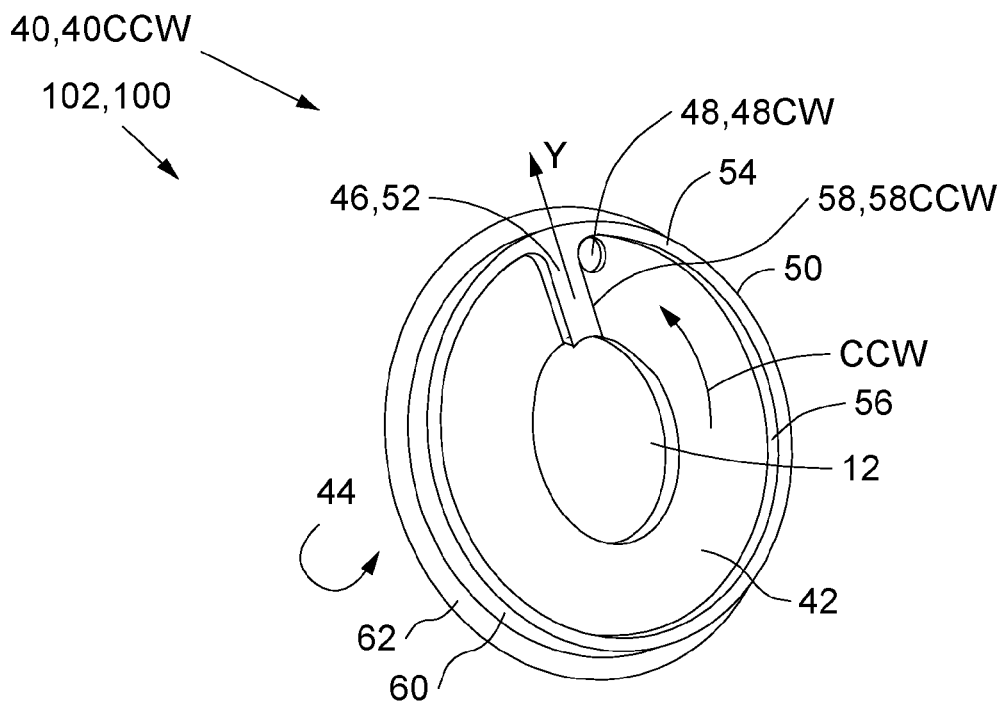
FIGS. 8 and 9 show a second and a third exemplary embodiment of an ejection device, and FIGS. 10 to 26 schematically illustrate various additional exemplary embodiments of disk structures and of ejection devices.

FIG. 8 illustrates a disk structure 100 which is configured as a second exemplary embodiment 102 of an ejection device 40 operative for use with a machine 10 driving a main flow MFF in counterclockwise direction CWW, as indicated by the arrow marked CCW. FIG. 8 is a mirror image of the front elevation of the distal circular side 42 of the clockwise ejection device 40CW shown in isometric view in FIG. 5, and depicts the counterclockwise ejection device 40CCW. By being a mirror image of the ejection device 40CW, the principle of operation of the counterclockwise ejection device 40CCW is the same as that of the clockwise ejection device 40CW described hereinabove, but operates in accordance with the counterclockwise direction CWW of the main flow MFF. With the ejection device 40CCW, the obstacle 46, or ridge 46, creates the zone ZSP at stagnation pressure and the fluid impinges on the counterclockwise blocking face 58CCW, which may be parallel to the counterclockwise blocking face 58CW. Typically, the counterclockwise blocking face 58CCW is perpendicular to the primary vortex flow rotating concentric to the shaft 14 in the seal chamber 28.

The discharge passage 48 or counterclockwise discharge passage 48CCW is evidently disposed adjacent and upstream of the obstacle 46, and has at least a portion thereof that is disposed in the zone ZSP of fluid at stagnation pressure created by the obstacle 46. Further description of the operation of the counterclockwise ejection device 40CCW is evidently not necessary. It is thus possible to implement an ejection device 40 matching a selected direction of the main flow MFF, either clockwise CW or counterclockwise CWW, as an ejection device, respectively 40CW or 40CCW.

Figure 9:
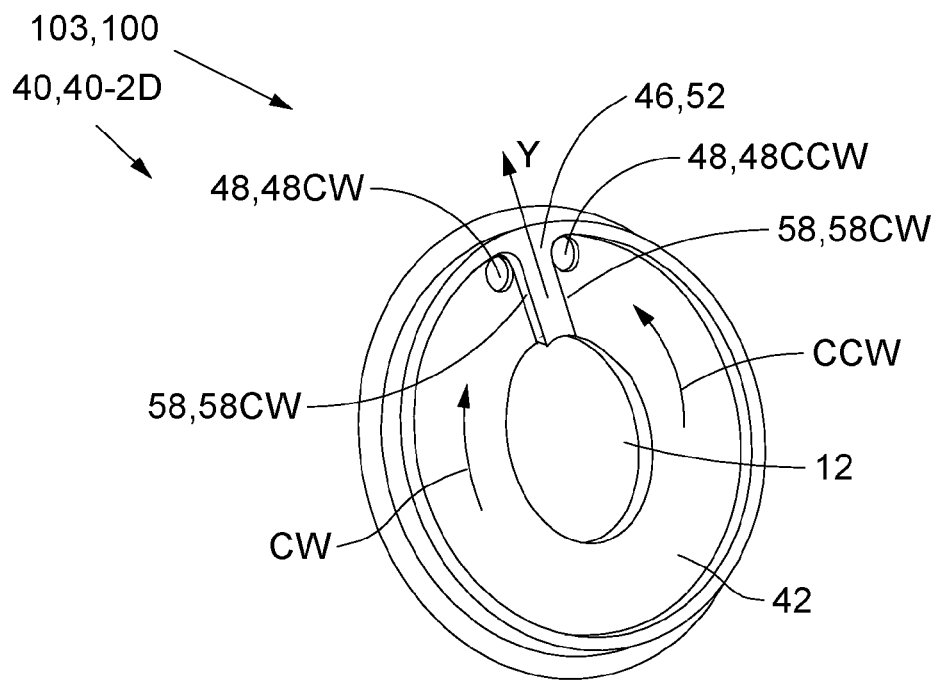

FIG. 9 depicts a third exemplary embodiment 103 of the ejection device 40, marked as 40-2D, which is operative with both a clockwise CW and a counterclockwise CCW direction of main flow MFF. The arrows marked CW and CCW indicate respectively, the clockwise and the counterclockwise direction of the main flow MFF. In FIG. 9, each one respective clockwise discharge passage 48CW and counterclockwise discharge passage 48CWW is disposed adjacent and upstream of the obstacle 46, and has at least a portion thereof which is disposed in the respective zone ZSP of fluid at stagnation pressure created by the obstacle 46. This means that with the clockwise main flow MFF, the clockwise discharge passage 48CW is operative with the clockwise flow blocking face 58CW which creates the clockwise zone ZSP. Likewise, with the counterclockwise main flow MFF, the counterclockwise discharge passage 48CCW is operative with the counterclockwise flow blocking face 58CCW and with the thereby created counterclockwise zone ZSP.

The operation of the bidirectional ejection device 40-2D is the same as first, the clockwise ejection device 40CW and second, the counterclockwise ejection device 40CCW, as described hereinabove, and therefore, further description is not necessary and needs not to be repeated. The bidirectional ejection device 40-2D is self-adaptable to the clockwise CW and to the counterclockwise CCW direction of the main flow MFF of fluid. 10

Additional Exemplary Embodiments

FIGS. 10 to 26 schematically illustrate exemplary embodiments of various disk structures 100 that are configured as ejection devices 40. In the FIGS. 10 to 26, upstream and downstream are relative to the primary clockwise vortex flow rotating in the seal chamber 28.

Figure 10:
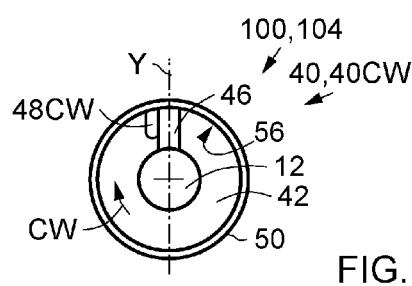
Figure 14:
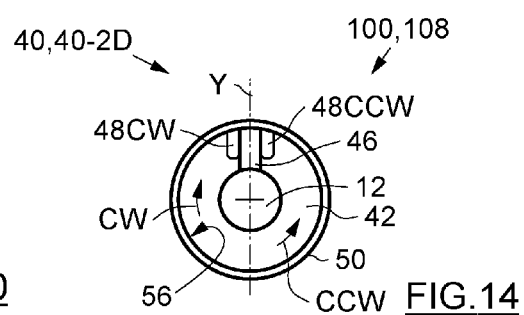

FIG. 10 depicts an exemplary embodiment 104 of a clockwise ejection device 40CW having a radially disposed obstacle 46 blocking some of the primary clockwise vortex flow flowing in the seal chamber 28. The obstacle 46 stretches radially away from the rim interior 56 and up to the shaft opening 12. The clockwise discharge passage 48CW is oblong rather than being configured as the circular bore 48B shown in FIG. 5, and is disposed upstream along and adjacent the obstacle 46, starting from the rim interior 56 and ending short of the shaft opening 12. An exemplary embodiment 104* of a counterclockwise ejection device 40CCW, not shown in the Figs. but similar to the embodiment 104, is obtained by taking a mirror image of the front elevation of the distal circular side 42 shown in FIG. 10.

Figure 11:
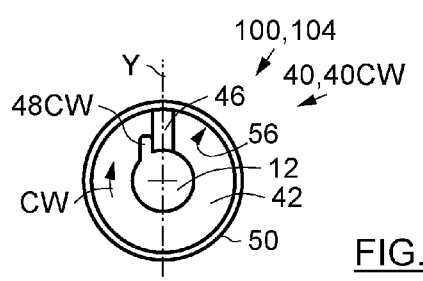
Figure 15:
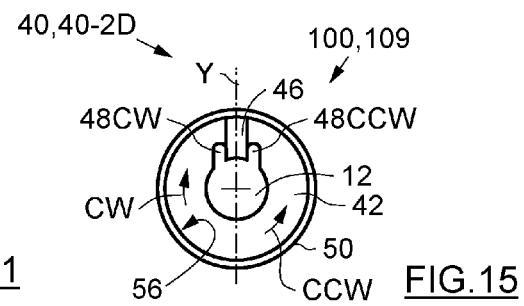

FIG. 11 illustrates another exemplary embodiment 105 of a clockwise ejection device 40CW having a radially disposed obstacle 46 blocking some of the primary clockwise vortex flow in the seal chamber 28. The obstacle 46 stretches radially away from the rim interior 56 up to the shaft opening 12. An oblong clockwise discharge passage 48CW stretches upstream along and adjacent the obstacle 46, starting from the shaft opening 12 and ending proximate the rim interior 56. An exemplary embodiment 105* of a counterclockwise ejection device 40CCW, not shown in the Figs. but similar to the embodiment 105 is obtained by taking a mirror image of the front elevation of the distal circular side 42 shown in FIG. 11.

Figure 12:
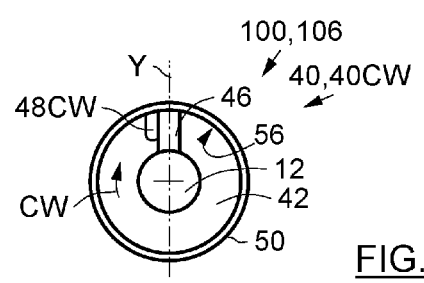
Figure 16:
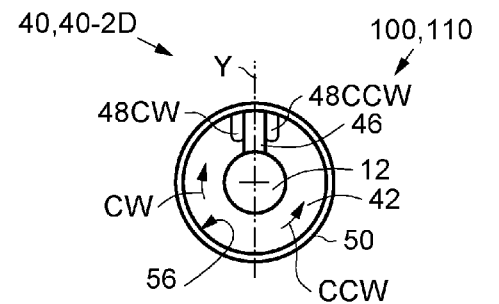

FIG. 12 shows yet another exemplary embodiment 106 of a clockwise ejection device 40CW having a radially disposed obstacle 46 blocking some of the clockwise vortex flow in the seal chamber 28. The obstacle 46 stretches radially away from the rim interior 56 and ends short of and away from the shaft opening 12. An oblong clockwise discharge passage 48CW is disposed upstream along and adjacent the length of the obstacle 46. An exemplary embodiment 106* of a counterclockwise ejection device 40CCW, not shown in the Figs. but similar to the embodiment 106, is obtained by taking a mirror image of the front elevation of the distal circular side 42 shown in FIG. 12.

Figure 13:
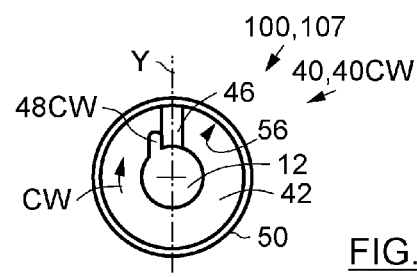
Figure 17:
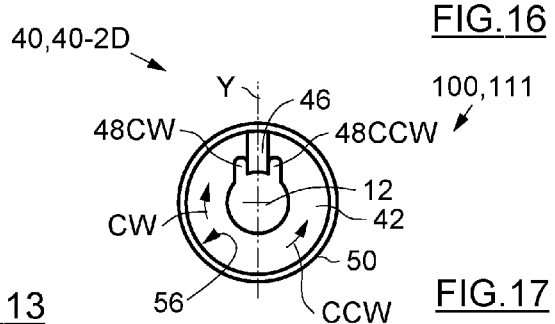

FIG. 13 illustrates yet another exemplary embodiment 107 of a clockwise ejection device 40CW having a radially disposed obstacle 46 blocking some of the primary clockwise vortex flow in the seal chamber 28. The obstacle 46 stretches radially away from the shaft opening 12 and ends short of and away from the rim interior 56. An oblong clockwise discharge passage 48CW is disposed upstream along and adjacent the length of the obstacle 46. An exemplary embodiment 107* of a counterclockwise ejection device 40CCW, not shown in the Figs. but similar to the embodiment 107, is obtained by taking a mirror image of the front elevation of the distal circular side 42 shown in FIG. 13.

FIGS. 14 to 17 depict other various exemplary embodiments 108 to 111 of bidirectional ejection devices 40-2D which are configured for operation with either a clockwise rotating or a counterclockwise rotating main flow MFF of fluid. The exemplary embodiments 108 to 111 are obtained by taking a mirror image about the axis Y of a front elevation showing the discharge passage 48CW of the distal circular side 42 of the embodiments 104 to 107 shown in FIGS. 10 to 13. The resulting mirror image illustrates bidirectional ejection devices 40-2D having each a clockwise discharge passage 48CW and a counterclockwise discharge passage 48CCW. The embodiments 108 to 111 are symmetric about their axis Y but asymmetric embodiments may also be practical. 30

Figure 18:
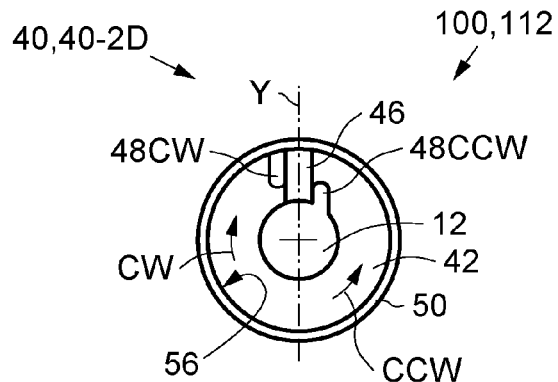
Figure 19:
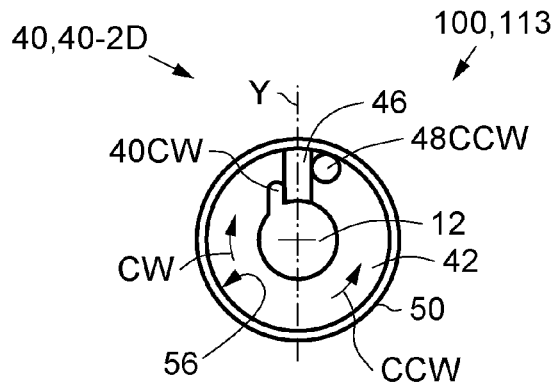

FIGS. 18 and 19 illustrate exemplary embodiments 112 and 113 of bidirectional ejection devices 40-2D, asymmetric about their axis Y due to the disposition of or the shape of the discharge passages 48CW and 40CCW, operative respectively with a clockwise CW or a counterclockwise CCW main flow MFF.

Figure 26:
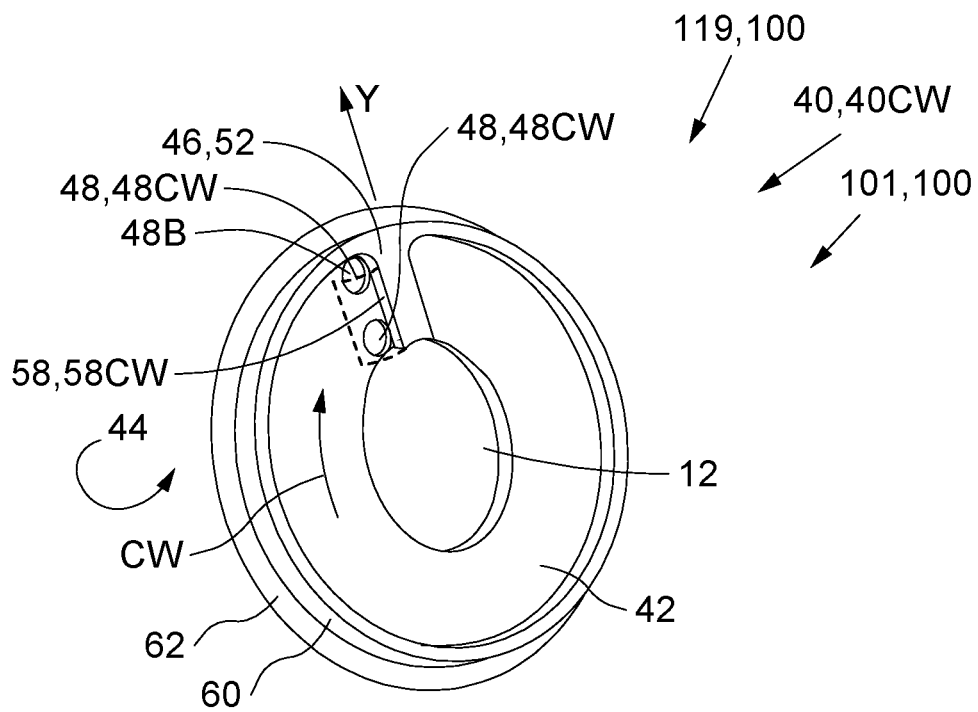

It is understood that in the present description the various discharge passages 48, 48CW, and 48CCW may be selected to have other geometrical shapes, different from the circular or oblong shapes depicted in the FIGS. If desired, more than one discharge passages 48, 48CW, and 48CCW may be associated with a same flow blocking face 58 pertaining to an obstacle 46, as shown for example in FIG. 26. An ejection device operative with a clockwise flow 40CW and/or a counterclockwise flow 40CCW may have more than one discharge passage 48. Likewise, an ejection device operative with a bidirectional flow of fluid may have one or more discharge passages 48 on each side of the obstacle 46. It is further understood that even though not shown in the Figs., except in FIG. 22, the obstacle 46 may have various shapes and sizes, but needs to have at least one flow blocking face 58.

Figures 20, 21:
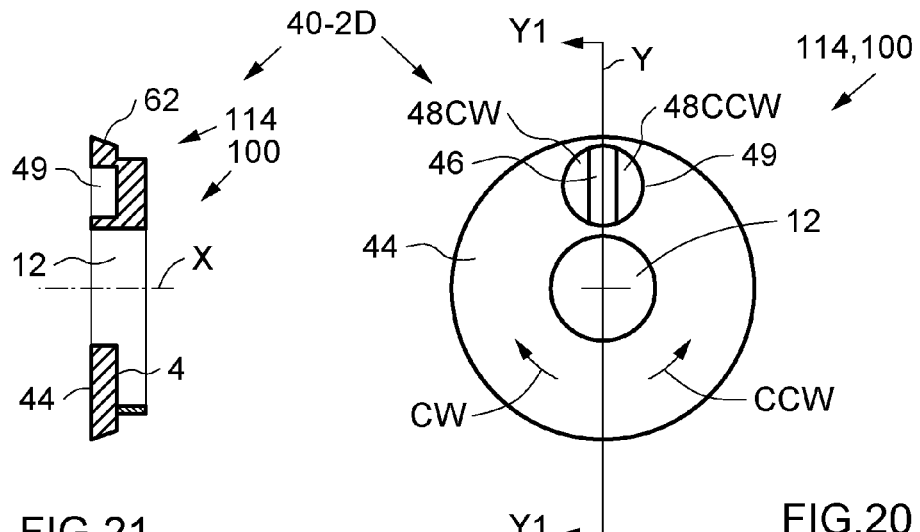

FIGS. 20 and 21 illustrate still one more exemplary embodiment 114 of an ejection device 40-2D where both the clockwise discharge passage 48CW and the counterclockwise discharge passage 48CCW share a same back-bore 49. FIG. 20 is a front elevation of the proximal circular side 44 showing the circular back-bore 49, and FIG. 21 is a cross-section of FIG. 20 taken along the axis of symmetry Y as a cut Y1-Y1, thus through and along the obstacle 46. The back-bore 49 extends throughout, from the proximal circular side 44 to the distal circular side 42, and may have a shape different from the circular shape, even though not being shown as such in the Figs. However, the length of the radially disposed obstacle 46 has preferably, but not necessarily, to be sufficiently long to bridge the back-bore 49. The discharge passage 48CW for clockwise flow and the discharge passage 48CCW for counterclockwise flow are both opened to provide fluid communication from the seal chamber 28 to the process side PS, thus through the distal circular side 42 and via the back-bore 49. If desired, the embodiments 108 to 111 may use such a back-bore 49. The operational functionality of the embodiment 114 remains the same as with the embodiments 108 to 113 described hereinabove.

Figure 22:
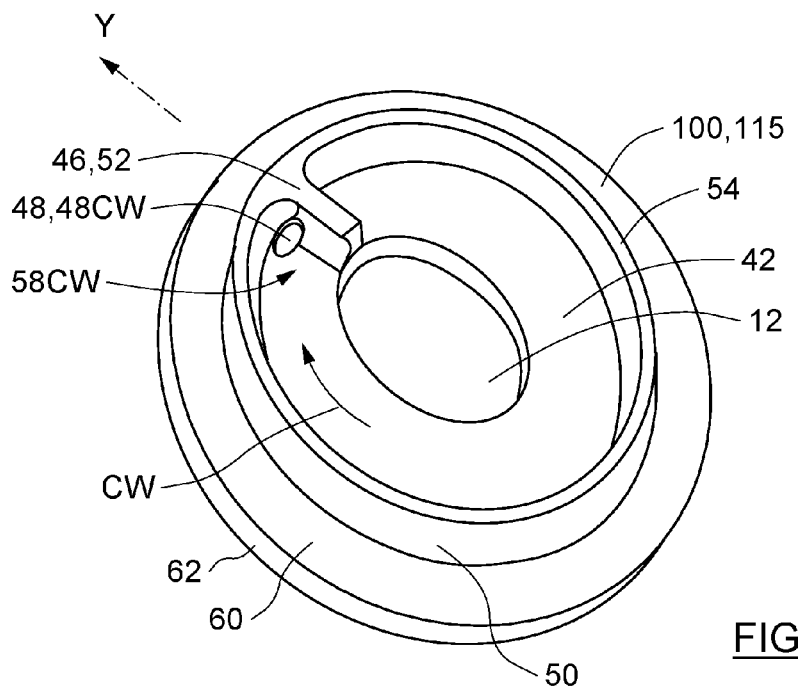

Evidently further combinations and configurations of the versatile disk structure 100 wherefrom the ejection device 40 is implemented, may also be practical. For example, instead of being configured as a flat planar surface, the flow blocking face 58 may be concave as shown in FIG. 22. Alternatively, the flat planar surface of the flow blocking face 58 may form an acute angle opposite the incoming flow of fluid.

FIG. 22 illustrates yet one more exemplary embodiment 115 of an ejection device 40. FIG. 22 depicts an exemplary disk structure 100 having an obstacle 46 with a blocking face 58CW which has been configured to become a clockwise ejection device 40CW by the addition of an upstream disposed discharge passage 48CW. The upstream flow blocking face 58CW of the obstacle 46 may be concave and may extend radially away from the rim interior 56 and up to the shaft opening 12 or stop short thereof. Although not shown in the Figs., a counterclockwise flow blocking face 58CCW may also be concave and a bidirectional ejection device 40-2D may feature an obstacle 46 with for example, one concave and one planar flow blocking face 58CW or 58CCW, or with two concave flow-blocking faces 58CW and 58CCW.

The various embodiments of the different ejection devices 40, namely 101 to 115, were configured for discharge of fluid out of the seal chamber 28 in the axial direction, i.e. parallel to the X axis shown in FIG. 7 for example. However, one may also consider radial discharge of fluid out of the seal chamber 28 by ejection of fluid perpendicular to the axial direction. An example of such an embodiment is shown in FIG. 23.

Figure 23:
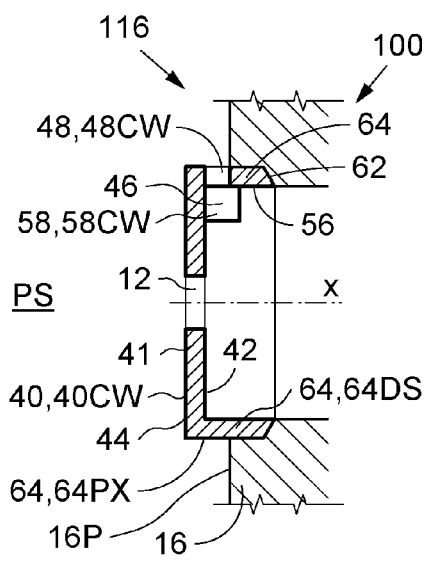

FIG. 23 illustrates an exemplary embodiment of a circular disk structure 100 which may be configured as an exemplary embodiment 116 of a clockwise ejection device 40CW for the radial ejection of fluid perpendicular to the X axis of the machine 10. FIG. 23 depicts the clockwise ejection device 40CW as a diametrical cross-section is taken through the radial discharge passage 48CW. Only the proximal exterior face 16P and a portion of the housing 16 are shown in FIG. 23 for the sake of clarity. In broad terms, the cup-like disk structure 100 has a rim wall 64 that extends from a circular bottom 41 which has a central shaft opening 12 for the passage therethrough of the shaft 14, not shown. The rim wall 64 has a distal rim wall portion 64DS which is disposed in the interior of the seal chamber 28, not shown, thus distal of the proximal exterior face 16P, and terminates distally in a bevel 62. As described hereinabove, the bevel 62 is provided to arrest further penetration of the ejection device 40 into the seal chamber 28. Obviously, the embodiment 116 of the clockwise ejection device 40CW may be coupled to the housing 16 by various methods and means known to those skilled in the art and needs not to be described in detail. The rim wall 64 also has a proximal rim wall portion 64PX which protrudes proximally out and away from the proximal exterior face 16P of the housing 16 and into the process side PS.

In FIG. 23, the clockwise discharge passage 48CW is opened radially, throughout the rim wall portion 64PX, for the radial ejection of fluid. The clockwise discharge passage 48CW for radial ejection provides fluid communication from the seal chamber 28, not shown, to the main flow MFF. The disposition of the clockwise discharge passage 48CW allows fluid containing contaminants CNT to be ejected radially into the process side PS perpendicular to the axis X and parallel to the proximal exterior face 16P of the housing 16, The radially-disposed obstacle 46 with the flow blocking face 58 is fixed to the distal circular side 42 downstream of the discharge passage 48, and stretches from the rim interior 56 to end short of, as shown in FIG. 23, or at the shaft opening 12. Therefore, the embodiment 116 which is thus configured for radial discharge, may have a clockwise ejection device 40CW and a discharge passage 48CW with a flow blocking face 58CW. Evidently, as described hereinabove, the disk structure 100 of the embodiment 116 may also be configured as a counterclockwise radial ejection device 40CCW and as a bidirectional radial ejection device 40-2D configured for operation with a main flow of fluid MFF that is respectively, counterclockwise and bidirectional. The principles described hereinabove for the implementation, use and manufacture of the embodiments 101 to 115 and 101* to 107* relative to axial ejection devices 40 may be applied to the implementation, use and manufacture of various radial ejection devices 40.

Figure 24:
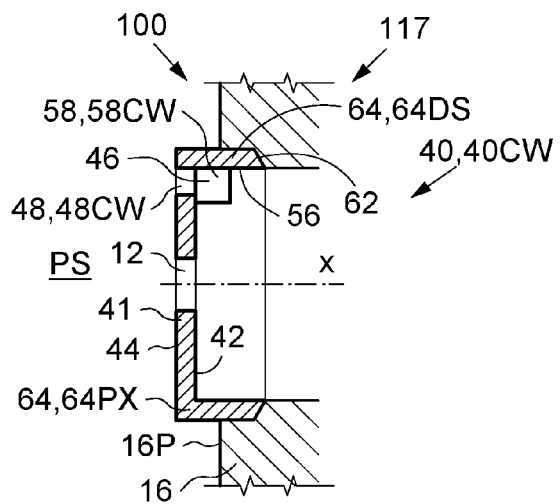

FIG. 24 depicts the same disk structure 100 used for the embodiment 116 but in a different configuration, namely as an exemplary embodiment 117 of an ejection device 40CW for axial ejection. The embodiment 117 illustrates a configuration wherein the discharge passage 48CW is disposed for axial ejection of fluid, thus parallel the X axis and perpendicular to the proximal exterior face 16P. The discharge passage 48CW is opened throughout the circular bottom 41, from the proximal circular side 44 to the distal circular side 42. Thereby, fluid communication is established from the seal chamber 28, not shown, to the main flow MFF. The radially-disposed obstacle 46 with the flow blocking face 58 is fixed to the distal circular side 42, downstream of the discharge passage 48, and may stretch from the rim interior 56 to end short of, as shown in FIG. 24, or at the shaft opening 12. Therefore, the embodiment 117 shown in FIG. 24 is a clockwise ejection device 40CW for axial ejection, having a discharge passage 48CW and a clockwise flow blocking face 58CW. As described hereinabove with respect to the embodiment 116, the disk structure 100 of the embodiment 117 may also be configured as a counterclockwise ejection device 40CCW and as a bidirectional axial ejection device 40-2D for axial ejection, configured for operation with a main flow of fluid MFF that is respectively, counterclockwise and bidirectional.

Although not shown as such in the Figs. the same disk structure 100 used for the embodiments 116 and 117 may be configured to eject contaminants CTN in both axial and radial direction simultaneously. To this end, at least two discharge passages 48 have to be opened in the disk structure 100 and be disposed upstream of the obstacle 46: one discharge passage 48 oriented as in the embodiment 116 and another discharge passage 48 oriented as in the embodiment 117. In other words, both discharge passages 48 are at least about perpendicular to each other and are disposed in at least a portion of the stagnation zone ZPS. Thereby contaminants CNT may be discharged perpendicular and along the X axis.

The same disk structure 100 for the implementation of the embodiments 116 and 117 may thus be held in stock or delivered to a user, not shown, as a versatile ejection device 40. Later, when needed, a supplier or a user, both not shown, may configure the disk structure 100 as desired, either as embodiment 116 or 117 possibly even in situ, by appropriate machining of one or more discharge passage(s) 48, to become an ejection device 40 for axial or radial ejection, for clockwise, counterclockwise, or bidirectional flow of fluid containing contaminants CNT.

Figure 25:
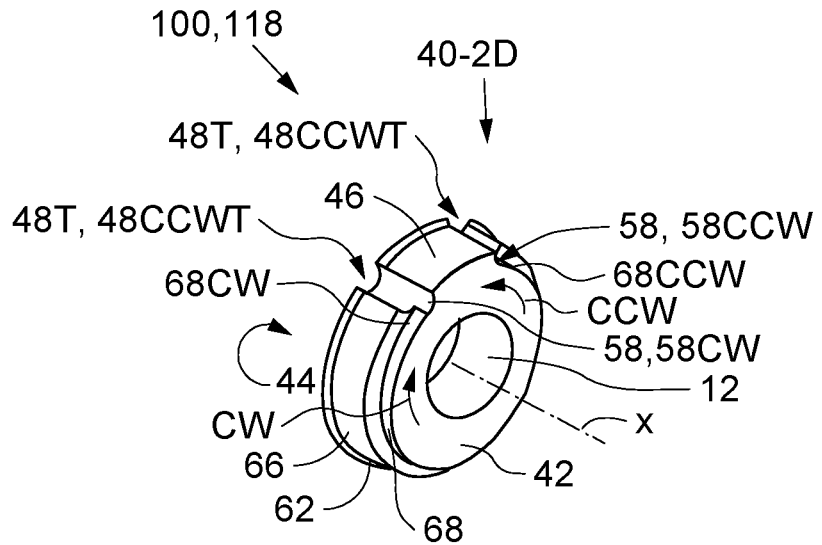

FIG. 25 illustrates an isometric view of an exemplary embodiment 118 of a bidirectional ejection device 40-2D. The purpose of the embodiment 118 is to emphasize the freedom of selection of the shape of the discharge passage(s) 48.

Similar to the embodiment 103 shown in FIG. 9, the embodiment 118 is annulus-like and has a concentric throughout shaft opening 12 and a planar distal circular side 42 facing the seal chamber 28, which is not shown. A planar proximal circular side 44 may have a largest exterior diameter that slopes radially distally to form a bevel 62 which ends on a mainly flat cylindrical exterior circumference 66 of medium diameter, smaller than the largest exterior diameter. The bevel 62 allows a typically flush assembly with, but not shown, the proximal exterior face 16P of the housing 16. Two passages 48T configured like troughs, namely 48CWT and 48CCWT, are cut parallel the X axis in the exterior periphery of the cylindrical exterior circumference 66 and in the bevel 62. In contrast with the various discharge passages 48 described hereinabove, a portion of the cross-section of a trough-like discharge passage 48T is open, but will become a closed periphery once mounted into the housing 16. The housing 16 receives the discharge passage 48T therein and completes to close the periphery of the discharge passage 48T.

Both discharge passages 48T may be separated apart by a short peripheral distance, i.e. by a sectorial angle of about 60° for example. A circumferential duct 68 is cut in the distal portion of the cylindrical exterior circumference 66, where the cut extends from the discharge passages 48CWT to the discharge passages 48CCWT, along the remaining complementary larger peripheral distance, i.e. with a sectorial angle of about 300°. The duct 68 provides a conduit for a portion of the fluid to impinge on a flow blocking face 58 of the obstacle 46: The obstacle 46 is formed over the short peripheral distance extending between a clockwise flow-blocking face 58CW disposed opposite a first end 68CW of the duct 68 and a second counterclockwise flow-blocking face 58CCW which is disposed opposite the other end of the duct 68.

In operation, fluid from the proximal region 15 of the seal chamber 28 will flow within the duct 68, impinge on the obstacle 46, create a zone ZSP at stagnation pressure, not shown, and be pumped through, but not shown, the discharge passage 48. From there the fluid will enter into the process side PS for exit with the main flow MFF. A disk structure 100 or an ejection device 40 may thus have a discharge passage 48 which is configured with a desired shape and with an open periphery, which periphery will be closed by the housing 16 once inserted therein.

FIG. 26 depicts an isometric view of a disk structure 100 which is configured as an exemplary embodiment 119 of a clockwise ejection device 40CW. The purpose of the embodiment 119 is to emphasize the freedom of selection of the number of discharge passage(s) 48. In contrast with the embodiment 101 shown in FIG. 5, two, thus more than one discharge passage 48CW are opened upstream of the obstacle 46. The arrow marked CW indicates the clockwise direction of rotation of the main flow MFF. To create a counterclockwise ejection device 40CCW as an exemplary embodiment 120, not shown in the Figs., it suffices to take a mirror image of the front elevation of the distal circular side 42 shown in FIG. 26. In general, the embodiment of a counterclockwise ejection device 40CCW may be obtained by taking a mirror image of the front elevation of the distal circular side 42.

Another exemplary embodiment 121 is obtained by taking a mirror image 5 about the axis Y of the portion of the front elevation showing the two discharge passages 48CW of the distal circular side 42 of the embodiments 119 shown in FIG. 26. The resulting mirror image illustrates a bidirectional ejection devices 40-2D having two clockwise discharge passages 48CW and two counterclockwise discharge passages 48CCW. In general, the embodiment of a bidirectional ejection device 40-2D may be obtained by taking a mirror image about the axis Y of the portion of the front elevation showing the discharge passage(s) 48CW of the distal circular side 42.

The embodiment 121 is symmetric about the axis Y but asymmetric embodiments may also be practical. For example, but not shown in the Figs., two clockwise discharge passages 48CW and one counterclockwise discharge passage 48CCW are one option. Likewise, one clockwise discharge passage 48CW and two counterclockwise discharge passages 48CCW present an additional option. Evidently, the number of discharge passages 48, either clockwise or counterclockwise opened in the embodiment 121 may be selected as desired. This means that yet more embodiments of an ejection device 40 may be made out of a disk structure 100 for one or more directions of rotation of the main flow MFF of fluid. An obstacle 46 may be incorporated in the disk structure 100 and may be configured to create a respective zone ZSP at stagnation pressure in the proximal region 15, not shown, for operation with both the clockwise CW and the counterclockwise CCW directions of flow of fluid. A plurality of discharge passages 48 may be opened in the disk structure 100 in at least a portion of each respective zone ZSP, clockwise and counterclockwise. This permits to create an ejection device 40 wherein at least two discharge passage 48 out of the plurality of discharge passages 48 are disposed upstream of the obstacle 46 for one direction of flow, say clockwise, and at least one discharge passage 48 is disposed upstream the obstacle 46 for the other direction of flow, say counterclockwise, Thereby, the disk structure 100 may be configured into an ejection device 40 which is self-adaptable to either one of the clockwise or counterclockwise directions of rotation of the main flow MFF.

It has thus been shown that a disk structure 100 may be configured as a pumping device 40 which may be implemented on the basis of the Pitot Effect to discharge contaminants CNT out of a seal chamber 28. It suffices to radially dispose an obstacle 46 in the disk structure 100 or in the ejection device 40, to form a flow blocking face 58 in the flow of fluid to create a zone at stagnation pressure ZSP wherein at least a portion of a discharge passage 48 is disposed. The number and the shape of the discharge passages 48 may be selected as desired or as dictated by functional necessity.

The assembly of an ejection device 40 to a machine 10 and the use of such an ejection device 40 are straightforward and therefore do not need to be described.

The many possible embodiments of the ejection device 40 may be made out of various materials ranging from plastic materials to metals. Well known processing methods for the production of the ejection device 40 for the various materials may include for example milling, forging, casting, injection molding, sintering, and 3-D printing.

An ejection device 40 may be supplied for operation with a clockwise flow, counterclockwise flow, or bidirectional flow of fluid, in a configuration denominated as respectively, ejection device 40CW, 40CCW, or 40-2D. Alternatively, there is provided a disk structure 100, which is an ejection device 40 without discharge passage(s) 48 therein. It may be said that a disk structure 100 is a blank ejection device 40 wherein a user is at liberty to enter one or more discharge passage(s) 48 of desired shape and number, where and when desired. Evidently, bidirectional ejection devices 40-2D are the most advantageous choice by being versatile and self-adaptive 25 to the direction of flow, thus beneficial for preventing mistakes related to flow direction incompatibility. It is also noted that a discharge passage 48 may be plugged or unplugged if and when desired.

Moreover, an ejection device 40 may be used to retrofit existing rotary machines 10, or be embedded therein ab initio in factory-produced rotary machines 10. In practice, the installation or retrofit of an ejection device 40 is straightforward to those skilled in the art and needs not to be described.

There have been described a method and ejection devices 40 for discharging or ejecting contaminants CNT out of a seal chamber 28 of a machine 10 which rotates and drives a main flow MFF of contaminated fluid. Such a result is achieved by the creation of a zone ZSP of fluid at stagnation pressure in the seal chamber 28. It is the stagnation pressure in the zone ZSP that ejects the contaminants CNT out of the seal chamber 28. The ejection of contaminants CNT is performed through at least one discharge passage 48, out of the seal chamber 28 and into the process side PS. The at least one discharge passage 48 may be disposed at least in portion in the zone ZSP. The discharge passage 48 provides fluid communication between the seal chamber 28 and the process side PS and thus fluid communication to the main flow of fluid MFF.

The zone ZSP is created by an obstacle 46 disposed in the seal chamber 28. In the seal chamber 28 there is a primary vortex flow of fluid and the discharge passage 48 is disposed in the vortex flow upstream of the obstacle 46. The obstacle 46 may be configured to have one or two flow blocking faces 58. A flow blocking face 58 is operative with a clockwise CW or a counterclockwise CCW direction of the main flow MFF of fluid.

An obstacle 46 may have at least one flow blocking face 58, i.e. a clockwise blocking face 58CW and/or a counterclockwise blocking face 58CWW. The clockwise blocking face 58CW is operative with a clockwise CW direction of rotation of the main flow MFF of fluid. Likewise, the counterclockwise blocking face 58CCW is operative with a counterclockwise CCW direction of rotation of the main flow MFF of fluid. The clockwise blocking face 58CW is operative with a clockwise discharge passage 48CW which is disposed upstream of the clockwise blocking face 58CW. Likewise, the counterclockwise blocking face 58CCW is operative with a counterclockwise discharge passage 48CCW which is disposed upstream of the counterclockwise blocking face 58CCW. Each one of the at least one clockwise blocking face 58CW and the counterclockwise blocking face 58CCW is operative with at least one discharge passage 48, respectively at least one clockwise discharge passage 48CW and at least one counterclockwise discharge passage 48CCW.

One may also say that there has been described a method, a disk structure 100 and ejection devices 40 for discharging or ejecting contaminants CNT out of a seal chamber 28 of a machine 10 which rotates and drives a main flow MFF of contaminated fluid.

In other words, there was described hereinabove a method for using a disk structure 100 and ejection devices 40 which close a proximal region 15 of the seal chamber 28 of a rotary machine 10 that drives a main flow MFF of fluid holding contaminants CNT. The ejection device 40 incorporates therein an obstacle 46 that is disposed in the proximal region 15 of the seal chamber 28 to create a zone ZSP of fluid at stagnation pressure when the seal chamber 28 is closed. The ejection device 40 also incorporates therein at least one discharge passage 48 which is disposed in at least a portion of the zone ZSP to couple the proximal region 15 and the main flow MFF in fluid communication. Thereby, when the seal chamber 28 is closed, the stagnation pressure ejects contaminants CNT out of the seal chamber 28 and into the main flow of fluid MFF via the discharge passage 48.

The mutual disposition of the zone ZSP and of the at least one discharge passage 48 is configured to operate with a main flow MFF which flows in a clockwise direction CW, or in a counterclockwise direction CCW, or in both a clockwise CW and a counterclockwise CWW direction.

Furthermore, the ejection device 40 incorporates therein an obstacle 46 that is configured to operate with a main flow MFF that flows in a clockwise direction CW, or in a counterclockwise direction CWW, or in both a clockwise CW and counterclockwise CCW direction. The obstacle 46 has at least one flow blocking face 58 which is configured to create a zone ZSP a stagnation pressure, for example with a blocking face 58 having a flat planar surface or as a concave surface.

There was also described an ejection device 40 made from a disk structure 100 wherein the ejection device 40 is configured to discharge contaminants CNT out of a seal chamber 28 including a proximal region 15 which is disposed in a machine 10 rotating fluid in a driven main flow MFF of fluid. The flow of fluid may be rotated into a clockwise CW or a counterclockwise CCW direction of rotation of the main flow MFF of fluid. The disk structure 100 incorporates therein an obstacle 46 which is configured to create a respective zone ZSP at stagnation pressure in the proximal region 15, for operation relative to and with both a clockwise CW or a counterclockwise CCW direction of rotation of the main flow MFF. A plurality of discharge passages 48 may be opened in the disk structure 100 for disposition in at least a portion of the zone ZSP to create an ejection device 40. The ejection device 40 may have at least two discharge passage 48 out of the plurality of discharge passages 48 that are disposed upstream of the obstacle 46 for one direction of flow, say the clockwise direction of rotation of the main flow MFF. Furthermore, at least one discharge passage 48 may be disposed upstream of the obstacle 46 for the other direction of flow, for example, the counterclockwise direction of rotation of the main flow MFF. The stagnation pressure in the zone ZSP is disposed upstream the obstacle 46 to eject contaminants CNT into the process side PS. Thereby the disk structure 100 may be configured into an ejection device 40 which is self-adaptable to the direction of rotation.

As described hereinabove, a disk structure 100 is configurable into an ejection device 40 and may be configured to close a proximal region 15 of a seal chamber 28 of a rotary machine 10 driving a main flow MFF of fluid holding contaminants CNT. At least one flow blocking face 58 may be configured to create a zone ZSP at stagnation pressure in the proximal region 15 relative to a clockwise CW or a counterclockwise CCW direction of rotation of the main flow. In addition, at least one discharge passage 48 may be opened in the disk structure 100 and may be disposed in at least a portion of the zone ZSP. Thereby, contaminants CNT are ejected through the at least one discharge passage 48 and into the main flow MFF. There is thus provided a method for implementing a disk structure 100 and an ejection device 40 that are self-adaptable, thus accommodate the direction of rotation of the main flow MFF. Moreover, there is provided a method, a disk structure 100 and ejection devices 40 that permit ejection of fluid in radial and/or in axial direction.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

INDUSTRIAL APPLICABILITY

The disk structure 100, the ejection device 40 and the method for use of the ejection device 40 are applicable in industries operating in the field of dynamic axisymmetric work-absorbing turbomachinery, or rotating-fluid equipment, such as compressors and pumps for example.

| Reference Signs List | |
| --- | --- |
| # | Item |
| A | counter current flow A |
| APR | aperture |
| B | spirally outward flow B |
| CHN | channel |
| CHN1 | channel |
| CHN2 | channel |
| CNT | contaminant |
| CW | clockwise |
| CCW | counterclockwise, anticlockwise |
| DIS | arrow indicating discharge fluid |
| F | free point in the flow of fluid |
| G | Gap |
| M | arrows indicating proximal flow pattern |
| MFF | main flow of fluid |
| MOT | motor |
| N | arrows indicating distal flow pattern |
| OP | opening |
| PD | proximal device |
| PLN | plane |
| PS | process side |
| RDG | ridge |
| S | point at stagnation in the flow of fluid |
| SCND | secondary flow of fluid |
| SP | solid particle |
| V | velocity |
| W | wall |
| X | longitudinal axis |
| ZSP | zone at stagnation pressure |
| 10 | machine or centrifugal pump |
| 12 | shaft opening |
| 14 | pump shaft |
| 15 | proximal region of the seal chamber 28 |
| 16 | pump housing |
| 16id | housing interior diameter |
| 16P | proximal exterior face of the housing 16 |
| 18 | impeller |
| 18D | distal face of the impeller 18 |
| 20 | pump suction inlet |
| 22 | pump discharge outlet |
| 24 | distal face of impeller 18 |
| 26 | seal(s) assembly |
| 28 | seal chamber |
| 30 | interstice |
| 40 | ejection device |
| 40CW | ejection device for clockwise flow |
| 40CCW | ejection device for counterclockwise flow |
| 40-2D | bidirectional ejection device |
| 41 | circular bottom |
| 42 | distal circular side |
| 44 | proximal circular side |
| 46 | obstacle or ridge |
| 48 | discharge passage |
| 48B | discharge bore |
| 48CW | discharge passage for clockwise flow |
| 48CWT | trough-like clockwise discharge passage |
| 48CCW | discharge passage for counterclockwise flow |
| 48CCWT | trough-like counterclockwise discharge passage |
| 48T | trough-like discharge passage |
| 49 | back-bore |
| 50 | circumferential rim |
| 51 | step height |
| 52 | ridge distal surface |
| 54 | rim distal face |
| 56 | rim interior |

-continued

Reference Signs List

| # | Item |
|---|---|
| 58 | flow blocking face |
| 58CW | flow blocking face for clockwise main flow |
| 58CCW | flow blocking face for counterclockwise flow |
| 60 | rim exterior surface |
| 62 | rim bevel |
| 64 | rim wall |
| 64DS | distal rim wall portion |
| 64PX | proximal rim wall portion |
| 66 | cylindrical exterior circumference |
| 68 | duct |
| 68CW | first end of the duct |
| 68CCW | second end of the duct |
| 100 | disk structure |
| 104*-107* | exemplary embodiments |
| 101-121 | exemplary embodiments |

I claim:

1. An ejection device configured to close a proximal region of a seal chamber of a rotary machine driving a main flow of fluid holding contaminants, the ejection device comprising:
a fluid pumping mechanism having a disk structure and at least one discharge passage, said disk structure including opposed substantially flat proximal and distal sides, and said at least one discharge passage extending through the opposed proximal and distal sides in an axial direction;
a circumferential rim protruding from the distal side of the disk structure and extending along a circumferential direction of the disk structure;
a shaft opening provided in the disk structure; and
only a single obstacle protruding from the distal side of the disk structure and adapted to be disposed in the proximal region of the seal chamber of the rotary machine, the obstacle extending along a radial direction of the disk structure from the circumferential rim to the shaft opening, and the obstacle being configured to create at least one zone of fluid at stagnation pressure,
wherein the at least one discharge passage is disposed in at least a portion of the at least one zone to couple the proximal region and the main flow in fluid communication,
wherein the obstacle has at least one of a clockwise blocking face and a counterclockwise blocking face operative with a clockwise and a counterclockwise direction of rotation of the main flow, respectively, and the obstacle is disposed downstream of the discharge passage which is disposed upstream of the at least one of the clockwise blocking face and the counterclockwise blocking face,
whereby the stagnation pressure pumps contaminants concentrated in the proximal region out of the seal chamber and into the main flow via the at least one discharge passage according to the direction of rotation.

2. The ejection device of claim 1, wherein a mutual disposition of the at least one zone and the at least one discharge passage is configured to operate with the main flow.

3. A rotary machine which rotates and drives a main flow of fluid holding contaminants, the rotary machine comprising:
a seal chamber; and
an ejection device disposed in the seal chamber, the ejection device being configured to close a proximal region of the seal chamber, and the ejection device comprising:
a fluid pumping mechanism having a disk structure and at least one discharge passage, said disk structure including opposed substantially flat proximal and distal sides, said distal side facing an interior of the seal chamber, and said at least one discharge passage extending through the opposed proximal and distal sides in an axial direction;
a circumferential rim protruding from the distal side of the disk structure and extending along a circumferential direction of the disk structure;
a shaft opening provided in the disk structure; and
only a single obstacle protruding from the distal side of the disk structure and disposed in the proximal region of the seal chamber of the rotary machine, the obstacle extending along a radial direction of the disk structure from the circumferential rim to the shaft opening, and the obstacle being configured to create at least one zone of fluid at stagnation pressure,
wherein the at least one discharge passage is disposed in at least a portion of the at least one zone to couple the proximal region and the main flow in fluid communication,
wherein the obstacle has at least one of a clockwise blocking face and a counterclockwise blocking face operative with a clockwise and a counterclockwise direction of rotation of the main flow, respectively, and the obstacle is disposed downstream of the discharge passage which is disposed upstream of the at least one of the clockwise blocking face and the counterclockwise blocking face, whereby the stagnation pressure pumps contaminants concentrated in the proximal region out of the seal chamber and into the main flow via the at least one discharge passage according to the direction of rotation.

4. The machine of claim 3, wherein the machine comprises a housing having a proximal exterior face, and wherein the proximal side of the ejection device is disposed flush with the proximal exterior face of the housing.

5. The ejection device of claim 1, wherein the disk structure is configured as a pumping device which operates based on a Pitot Effect.

6. The ejection device of claim 1, wherein the blocking face has at least one of a flat planar surface, a concave face, and a face which forms an acute angle opposite to an incoming direction of the main flow.

7. An ejection device configured to close a proximal region of a seal chamber of a rotary machine driving a main flow of fluid in one of a clockwise and counterclockwise direction of rotation, said main flow of fluid holding contaminants, the ejection device comprising:
a disk structure comprising a circumferential rim protruding from one of opposed sides of the disk structure and extending along a circumferential direction of the disk structure, and a shaft opening formed through the disk structure;
only a single obstacle configured to be disposed in the proximal region of the seal chamber to create at least one zone at stagnation pressure, said single obstacle extending along a radial direction of the disk structure from the circumferential rim to the shaft opening thereof; and at least one discharge passage which is disposed in at least a portion of the at least one zone to couple the proximal region and the main flow in fluid communication, wherein said single obstacle has a clockwise blocking face and a counterclockwise blocking face respectively operative with the clockwise and the counterclockwise direction of rotation of the main flow, said single obstacle being disposed downstream of the discharge passage and the discharge passage being disposed upstream of the clockwise blocking face and the counterclockwise blocking face, whereby the stagnation pressure pumps contaminants concentrated in the proximal region out of the seal chamber and into the main flow via the at least one discharge passage according to the direction of rotation.

8. The ejection device of claim 7, wherein said at least one discharge passage is configured to discharge contaminants in at least one of a radial direction perpendicular to a longitudinal axis which extends through a center of the ejection device, and an axial direction.

9. The machine of claim 3, wherein the machine comprises a shaft disposed along a longitudinal axis of the machine, and wherein the at least one discharge passage is configured to discharge contaminants in at least one of a radial direction perpendicular to the longitudinal axis and the axial direction, which is a direction along the longitudinal axis.

10. The ejection device of claim 1, wherein an axis along which the discharge passage extends is parallel to a central axis of the ejection device.

11. The ejection device of claim 1, wherein a maximum diameter of a proximal side face of the ejection device is greater than a maximum diameter of a distal side face of the ejection device.

12. The ejection device of claim 1, wherein the at least one of the clockwise blocking face and the counterclockwise blocking face comprises a flow blocking face.

13. The ejection device of claim 1, wherein the shaft opening is provided in the disk structure at a position inward of the circumferential rim along the radial direction.

* * * * *